United States Patent [19]

Patroni et al.

[11] Patent Number: 5,008,377

[45] Date of Patent: * Apr. 16, 1991

[54] PRODUCTION OF PROTEINS IN ACTIVE FORMS

[75] Inventors: Joseph J. Patroni, West Preston; Malcolm R. Brandon, Ivanhoe, both of Australia

[73] Assignee: Bunge (Australia) Pty. Ltd., Melbourne, Australia

[ * ] Notice: The portion of the term of this patent subsequent to Jan. 10, 2006 has been disclaimed.

[21] Appl. No.: 184,342

[22] Filed: Apr. 21, 1988

[30] Foreign Application Priority Data

Apr. 21, 1987 [AU] Australia .............................. PI 1508

[51] Int. Cl.$^5$ .......................... C07K 3/22; C07K 3/28; C07K 15/14; C07K 15/26
[52] U.S. Cl. .................................... 530/416; 530/408; 530/409; 530/410; 530/412; 530/417; 530/420; 530/423; 530/350; 530/351; 530/397; 530/399; 435/69.1
[58] Field of Search ............... 530/408, 409, 410, 412, 530/416, 417, 420, 423, 350, 399, 351, 397, 399, 350; 435/68, 69.1

[56] References Cited

U.S. PATENT DOCUMENTS

| 4,677,196 | 6/1987 | Rausch et al. | 530/412 |
|---|---|---|---|
| 4,748,234 | 5/1988 | Dorin et al. | 530/412 |
| 4,797,474 | 1/1989 | Patroni et al. | 530/351 |

FOREIGN PATENT DOCUMENTS

86/05809  10/1986  World Int. Prop. O. .

OTHER PUBLICATIONS

Osterman, Lev A., *Methods of Protein and Nucleic Acid Research*, vol. 1, Springer Verlag, N.Y., 1984, pp. 69–71.
Pharmacia Biotechnology Products Catalog, 1986, pp. 6–11.

*Primary Examiner*—Margaret Moskowitz
*Assistant Examiner*—Keith C. Furman
*Attorney, Agent, or Firm*—Merchant, Gould, Smith, Edell, Welter & Schmidt

[57] ABSTRACT

A method for the preparation of a protein in a physiologically active or native form, which method includes
  providing a source of protein in a solubilized form, and a cationic exchange medium;
  contacting the source of protein and cationic exchange medium; and
  recovering the protein in a physiologically active form.

6 Claims, No Drawings

PRODUCTION OF PROTEINS IN ACTIVE FORMS

BACKGROUND OF THE INVENTION

The present invention relates to a method for the preparation of a protein in a biologically active or native form.

Recombinant DNA technology provides potentially extremely valuable means of synthesizing amounts of desirable eukaryotic (usually mammalian) proteins such as hormones, interferons, and enzymes. Although it has proved to be relatively easy to manipulate organisms such as bacteria to produce the desired protein, the host organism does not normally secrete the over-produced protein product into the culture medium. Thus lysis of the organisms (for example bacteria), followed by isolation of the desired protein is usually necessary.

A protein exists as a chain of amino acids linked by peptide bonds. In the normal biologically active form of such a protein or its native form as it is commonly referred to, the chain is folded into a thermodynamically preferred three dimensional structure, the conformation of which may be maintained by steric interaction intermolecular and intramolecular forces such as hydrogen bonding, hydrophobic interactions and charge interactions. In the prior art, the usual aggregation and insolubility under folding conditions of fully, or partially, unfolded proteins requires that folding be carried out in the presence of denaturants, reducing agents and in very dilute solutions, consequently, in large volumes. The handling of such dilute solutions and large volumes together with toxic reducing agents such as B-mercaptoethanol adds significantly to the cost when such processes are applied industrially.

In U.S. Pat. No. 4,797,474, the disclosure of which is herein incorporated by reference, applicants have described a highly economical method for the recovery of proteins in a soluble form from an insoluble protein source utilizing a cationic surfactant. Whilst this process allows for the efficient recovery of proteins in a soluble form, the proteins may not exhibit their normal biological activity. The proteins so recovered may not be in their native form.

Accordingly, it is an object of the present invention to overcome, or at least alleviate, one or more of the difficulties related to the prior art.

SUMMARY OF THE INVENTION

Accordingly, in a first aspect, there is provided a method for the preparation of a protein in a physiologically active or native form, which method includes
providing a source of protein in a solubilized form, and a cationic exchange medium;
contacting the source of protein and cationic exchange medium; and
recovering the protein in a physiologically active form.

The cationic exchange medium may be of any suitable type. The cationic exchange medium may be a cationic exchange resin. The cationic exchange resin may be a beaded cationic exchange resin. The cationic exchange resin may be equilibrated with any suitable cation or mixtures thereof. For example, NaCl or NaOH may be used.

The cationic exchange resin may be of any suitable type. An alkali metal or ammonium cationic exchange resin may be used. An $Na^+$ or $NH_4^+$ cation exchange resin may be used. A resin which generates a rapid ion exchange rate is preferred. For example the ion exchange process may be completed within several hours rather than days. Accordingly, a high porosity, high capacity resin is preferred. After equilibration, a nuclear sulfonic acid cationic exchange resin of the macroporous type sold under the trade designation "DOWEX" and available from The Dow Chemical Company has been found to be suitable. In particular DOWEX 50W-H (represents the hydrogen form (H) of a cationic, sulfonic acid, polystyrene exchange resin with divinyl benzene crosslinking) and DOWEX 50W×4 (50-100 mesh) (represents the hydrogen form of the polystyrene exchange resin with 4% divinyl benzene crosslinking and a mesh size grading of 50-100) have been found to be particularly suitable.

A particular advantage of the use of a cationic exchange medium in the method according to the present invention is the ability to regenerate the medium as required.

The cationic exchange resin may be provided in the form of a cationic exchange chromatography column or a mixing vessel. The source of protein may be contacted therewith via elution through the chromatography column or mixing vessel.

Whilst the mechanism of renaturation is complex, in part, the treatment with the appropriate cationic exchange media removes organic cations present or formed during the solubilisation and substitutes therefor other cations, the protein product of which is rapidly produced as a solution in a physiologically acceptable solvent and is in a physiologically active form.

It will be understood that, in its preferred aspect, the method according to the present invention provides a mechanism for the recovery of proteins via a single recovery step, once the proteins have been solubilised. This represents a significant improvement in efficiency, and thus cost, since steps such as dialysis or chemical refolding treatments may thus be avoided.

The pH at which the method according to the present invention is conducted may be varied depending on the optimum solubility characteristics of the protein selected. The pH may also be selected from about pH 2.5 to about pH 12.5.

The source of protein in a solubilised form may be provided by the treatment of the insoluble form with an aqueous cationic surfactant and/or polar organic solvent as described in U.S. Pat. No. 4,797,474, the entire disclosure of which is incorporated herein by reference. The solubilized protein may accordingly be provided from a source of insoluble protein including protein aggregates. The present invention is particularly applicable to biologically active proteins synthesised by microorganisms and eukaryotic cell lines which have been modified by recombinant DNA technology. The protein aggregate may comprise an inclusion body isolated by disruption or lysis of a host cell which may have been transformed or transfected with a vector including a gene coding for the protein. However it is not restricted thereto. In addition the present invention is applicable to naturally occurring precipitated protein complexes.

The protein aggregates which may be recovered according to the present invention may be selected from inclusion bodies and cytoplasmic aggregates. The inclusion bodies may be selected from biologically active polypeptides and peptides including growth hormones such as porcine, ovine and bovine growth hormones, interferons, immunogens and lymphokines, or synthesised heterogeneous or homogeneous polymers thereof.

The recovery step according to the present invention may include treating the product of the contact step to recover the protein. The treatment step may include a filtration step. In the preferred form, where the cationic exchange medium is in the form of a cationic exchange chromatography column, it will be understood that the contact and recovery steps may be combined.

The source of protein in a solubilised form may be contacted with the cationic exchange resin in any suitable manner. The source of protein may be utilised in a concentrated form. The source of protein may be present in an amount of approximately 1 to 200 mg/ml, preferably approximately 90 to 150 mg/ml.

DETAILED DESCRIPTION OF THE PREFERRED EMBODIMENT

In a preferred aspect the method according to the present invention further includes the step of mixing the physiologically active protein with a physiologically acceptable solvent. The physiologically acceptable solvent may be water or other dilute aqueous solution. A buffered aqueous solution is preferred.

Surprisingly, it has been found that after the treatment according to the method of the present invention, the solubilised protein is rendered soluble in the physiologically acceptable solvent solution and is converted into its physiologically active form.

In the method for the recovery of proteins in a solubilised form, utilising a cationic surfactant as described in Australian Patent Application 66874/86 it is preferred that the solubilised protein be separated from the resulting solution. The separation step may be selected from molecular differentiation procedures such as differential elution of the solubilised protein through a chromatographic medium, dialysis, ultrafiltration, differential precipitation, or ligand specific isolation. Whilst such a separation step may be used in conjunction with the method according to the present invention, in contradistinction to the prior art the present invention substantially simplifies this step as it may be conducted after the crude protein is converted into a physiologically active form, and the eluant or liquid medium used may be water or other dilute aqueous solution e.g. an aqueous buffer.

The method may be conducted at any suitable temperature above the freezing point of the solution. Preferably a temperature in the range of approximately 4° to 40° C. more preferably 4° to 10° C. may be used.

In a further aspect of the present invention, there is provided a pharmaceutical composition including a protein in a physiologically active or native form when prepared by the method as described above.

The pharmaceutical composition may further include a physiologically acceptable carrier or recipient. The carrier or recipient may be a solvent. The pharmaceutical composition may be a veterinary composition.

In the present invention it will be understood that in a preferred aspect the protein is produced in a physiologically active or native form and in a physiologically acceptable soluent.

The present invention will now be more fully described with reference to the accompanying examples. It should be understood, however, that the description following is illustrative only and should not be taken in any way as a restriction on the generality of the invention described above.

EXAMPLE 1

Crude inclusion bodies (600g wet weight) containing methionyl 1-190AA porcine growth hormone were isolated by conventional disruption of modified *E.coli*. The inclusion bodies were washed three times with a solution of 5TRITON X-100 ($\alpha$-(4-(1,1,3,3,-tetramethylbutyl) phenyl)-omega-hydroxypoly(oxy-1,2-ethanediyl)); and 5mM EDTA, and finally three times with aqueous 5mM EDTA: Vigorous agitation of the washed inclusion bodies in the presence of a solution of cetyl trimethylammonium bromide (500ml of 18.5% w/v) 0.15M TRIZM (Tris(hydroxymethyl) aminomethane) (pH 10.0, 50mM EDTA and dithiothreitol (5% w/v) resulted in complete solubilisation of the insoluble growth hormone. During the solubilisation the pH of this solution was kept constant (pH 10.0) by addition of some 1M sodium hydroxide.

The mixture was then clarified by centrifugation (25,000g, 30min), and the clear, pale yellow supernatant diluted (1:10) with water. The solution was then poured onto neutral DOWEX 50W33 1 (50-100 mesh) (represents the hydrogen form of the polystyrene exchange resin with 1% divinyl benzene crosslinking and a mesh size grading of 50-100); ion exchange resin, and the mixture placed into a roller bottle (2L, 15°). The liquid was then isolated by filtration, and was found to contain the growth hormone after substantially complete recovery. The soluble preparation containing significant quantities of cellular proteins as impurities was shown to be biologically active in the rat tibia bioassay (Table 1).

EXAMPLE 2

The method of Example 1 was repeated in the absence of reducing agent. Reducing agents are preferably avoided due to their toxicity and volatility.

An experiment was conducted wherein washed inclusion bodies (100g, wet weight) containing methionyl 1-190AA porcine growth hormone were vigorously agitated (2L) in the presence of cetyltrimethylammonium chloride (200ml, of 200% w/v), 0.15M TRIZMA (pH 10.0) and 40mM EDTA. The pH of the solution was kept constant throughout solubilisation.

The mixture was then immediately clarified by centrifugation (25,000g, 30 min), and the clear supernatant diluted 1:10 with water. The solution was then poured onto neutral, moist DOWEX 50W×4(50-100 mesh) (regenerated sodium form) ion exchange resin (400ml), the mixture placed into a conical flask and agitated (2L, 25°). The liquid was then isolated by decantation and was found to contain the growth hormone in a soluble form. The soluble preparation contained significant quantities of other proteins as impurities but was shown to be biologically active in the rat tibia bioassay (Table 1).

EXAMPLE 3

Crude inclusion bodies (600g wet weight) containing mehionyl 1-190AA porcine growth hormone were isolated and washed as described in Example 1. The inclusion bodies were then thoroughly agitated with cetyltrimethylammonium chloride (500ml of 18.5% w/v), 0.15M TRIZMA (pH 10.0), 50mM EDTA and dithiothreitol (3% w/v) resulted in complete solubilisation of the insoluble growth hormone. During the solubilisation the pH of this solution was maintained constant (pH 10.0) by addition of some 1M sodium hydroxide.

The mixture was then clarified by centrifugation (25,000g, 30 min.), and the clear, supernatant diluted (1:4) with 5M Urea 0.05M glycine (pH 11.0). The solution was immediately poured onto preequilibrated neutral DOWEX 50W×1(50–100 mesh) (sodium form), ion exchange resin (1.5L) and the mixture placed into a roller bottle (2L, 20°). The liquid was then isolated by filtration and subjected to dialysis with 0.05M TRIZMA (pH 10.0, 1hr, 4°) in an Amicon CH2H concentrator equiped with an S10 Y3 spiral wound cartridge. The solution containing the growth hormone was then allowed to stand at 4° C. for 16h prior to loading on a preequilibrated anion exchange chromatography support (Whotman DE 52). Chromatography then produced by elution at 60 ml/min with a solution of 0.05 TRIZMA pH 9.8 and an increasing sodium chloride gradient to a final 0.07M. Fractions containing pure growth hormone were then isolated and pooled. This purified growth hormone was found to be biologically active in a rat tibia bioassay (Table 1).

EXAMPLE 4

An experiment was conducted with 4–190AA porcine growth hormone substantially as indicated in Example 1. Again the final solution as obtained by filtration after contact with the resin was shown to be biologically active in the rat tibia bioassay (Table 1).

EXAMPLE 5

An experiment was conducted where the final solution obtained after contact with the cation exchange resin as described in Example 1 above, was directly applied to an ion exchange column (DEAE Fast Flow 11cm+30cm) at pH 11.0, and pure growth hormone was obtained after elution of the column with increasing ionic strength. This purified growth hormone was found to be biologically active in a rat tibia bioassay (Table 1).

EXAMPLE 6

An experiment was conducted with crude inclusion bodies (50mg) containing the D1 fragment of the 32kDa structural protein from infectious bursal disease virus which were sequentially washed (x3) with aqueous TRITON X- 100 (5%), 5mM EDTA and aqueous EDTA. The inclusion bodies were vigorously agitated with an aqueous solution containing a mixture of cetyl-trimethylammonium bromide (0.5ml of 18.5% w/v) and cetylpyridinium chloride monohydrate (0.5ml of 12% w/v), 0.15M TRIZMA (pH 10.0), 50mM EDTA and dithiothreitol (5% w/v). After 1 hour the mixture was centrifuged (25,000g, 30min). The clear supernatant was then diluted 1:4 with 5M urea, 0.05M glycine (pH 11.0) and the solution poured onto pre-equilibrated DOWEX 50W×1(50–100 mesh) (sodium form) ion exchange resin (10ml) and the mixture placed into a roller bottle (1h, 25°. The liquid was then isolated by filtration.

An immuno-dot blot analysis of the final physiologically acceptable solution using nitro-cellulose paper and a monoclonal antibody to the D1 polypeptide confirmed the antigenicity of the fused polypeptide.

| Treatment Group | Biological* Activity (%) |
|---|---|
| Example 1 | 27 |
| Example 2 | 24 |
| Example 3 | 94 |
| Example 4 | 30 |
| Example 5 | 90 |

Finally, it is to be understood that various other modifications and/or alterations may be made without departing from the spirit of the present invention as outlined herein.

We claim:

1. A method for the preparation of a protein in a soluble and physiologically active form from which organic cations have been removed, comprising:
   providing a source of protein, selected from the group consisting of growth hormones, interferons, immunogens and lymphokines, in a solubilized form, wherein the source of protein in the solubilized form is obtained by treating insoluble protein aggregates with an aqueous cationic surfactant, and wherein said cationic surfactant includes an organic cation selected from the group consisting of cetyl trimethylammonium cations, cetyl pyridinium cations, tetradecyl trimethylammonium cations, dodecyl trimethylammonium cations, mixed n-alkyl dimethyl benzyl ammonium cations, N, N-dimethyl-N-(2-(2-(4-(1,1,3,3,-tetramethyl butyl)-phenoxyl)ethoxy)ethyl)benzenemethanaminium cations;
   contacting said source of solubilized protein with a nuclear sulfonic acid cationic exchange resin, wherein the counter ion of said cationic exchange resin is an alkali metal; and
   recovering the protein in a soluble and physiologically active form from which organic cations have been removed.

2. The method of claim 1 wherein the cationic exchange resin is selected from the group consisting of DOWEX 50W-H, DOWEX 50×4, and DOWEX 50W×1 exchange resins.

3. The method of claim 2 wherein the cationic exchange resin is provided in the form of a cationic exchange chromatography column, and wherein the source of protein is contacted therewith by elution of the chromatography column with a mixture of the source of protein and a physiologically acceptable solvent.

4. The method of claim 3 wherein the source of protein is present in a concentration of approximately 1 to 200 mg/ml.

5. The method of claim 1 further comprising:
   mixing the product of the contacting step with a physiologically acceptable solvent selected from the group consisting of water and dilute aqueous buffer solutions, wherein the product of the contacting step is rendered soluble in the physiologically acceptable solvent; and
   separating the protein from the resulting solution after removing the organic cations from the solution.

6. The method of claim 5 wherein the separating step is accomplished by differential elution of the solubilized proteins through a chromatographic column, dialysis, ultrafiltration or differential precipitation, and wherein the eluant or liquid medium is water or other dilute aqueous buffers.

* * * * *